United States Patent
Rubow et al.

[11] Patent Number: 6,080,435
[45] Date of Patent: *Jun. 27, 2000

[54] METHOD AND SYSTEM FOR DISINFECTION AND STERILIZATION OF FOODSTUFFS AND MACHINERY

[76] Inventors: Ulrik Rubow, Johannesmindevei 24; Thure Carnfeldt, Barsoe, Bakkevaenget 7, both of DK-9000 Aalborg, Denmark

[ * ] Notice: This patent is subject to a terminal disclaimer.

[21] Appl. No.: 09/308,659

[22] PCT Filed: Dec. 3, 1996

[86] PCT No.: PCT/DK96/00505

§ 371 Date: Jun. 2, 1999

§ 102(e) Date: Jun. 2, 1999

[87] PCT Pub. No.: WO98/24333

PCT Pub. Date: Jun. 11, 1998

[51] Int. Cl.⁷ .............................. A23L 3/005; A23L 3/24; B65B 1/04; B65B 3/04
[52] U.S. Cl. .......................... 426/235; 426/326; 426/521; 99/477; 99/536; 422/299; 312/31.01
[58] Field of Search ..................... 426/320, 326, 426/511, 521, 235; 99/477, 536; 422/7, 26, 292, 297, 299; 312/31.01

[56] References Cited

U.S. PATENT DOCUMENTS

| | | | |
|---|---|---|---|
| 4,830,278 | 5/1989 | Khomura et al. | 99/468 |
| 4,865,857 | 9/1989 | Inagaki | 426/241 |
| 4,915,606 | 4/1990 | Shimokawa | 422/295 |
| 5,711,981 | 1/1998 | Wilson et al. | 426/511 |
| 5,902,619 | 5/1999 | Rubow et al. | 426/235 |

*Primary Examiner*—Nina Bhat
*Attorney, Agent, or Firm*—Dennison, Scheiner, Schultz & Wakeman

[57] ABSTRACT

A method and installation for disinfection or sterilization of food articles or machinery, in which the item of food or machinery to be disinfected or sterilized is electrically grounded, and vapor from water or other liquid substance is generated and directed through an electrostatic potential field of defined shape generated with an electrostatic high voltage, whereby the vapor assumes the shape of the field with an electrostatic potential imposed thereon. The grounded item is exposed to the charged vapor for a predetermined time at a temperature above 50° C.

14 Claims, 5 Drawing Sheets

METHOD AND SYSTEM FOR DISINFECTION AND STERILIZATION OF FOODSTUFFS AND MACHINERY

This application is a 371 National Stage Application of PCT/DK96/00505 filed Dec. 3, 1996.

BACKGROUND OF THE INVENTION

This present invention is concerned with a method for disinfection or sterilization of foods such as meat or vegetable products or produce, and of feed or machinery and equipment for food and feed production.

Such a method is known from the applicants' Danish Patent Application No. 1377/94.

It is the disadvantage of this known method that the solutions or mists of oxidizing substances used therein which impose on the aqueous solution a redox potential may cause, in critical circumstances, corrosion on machine pans and oxidization of surfaces with chemically reduced surface components, e.g. colors or dyes. Besides this, methods of disinfection are preferred in certain geographical areas which utilize no other means than pure water and thermal influence.

SUMMARY OF THE INVENTION

It is an object of the invention to overcome the drawbacks of the known methods.

By using the method according to the present invention, articles of food are disinfected/sterilized, such that humans and animals are protected from pathological reactions, poisonings and illnesses, and at the same time the attacks of corrosion mentioned above are reduced or prevented.

This present invention also encompasses an apparatus or installation designed to implement the method in accordance with the invention.

BRIEF DESCRIPTION OF THE DRAWINGS

In the following the invention will be described in more detail with references to the drawings, in which.

DESCRIPTION OF THE PREFERRED EMBODIMENTS

Most infections of a nature as described above are caused and started by surface growth of micro organisms on articles of food, feeds, or surfaces of other substances to which micro organisms can adhere.

Figure 1:
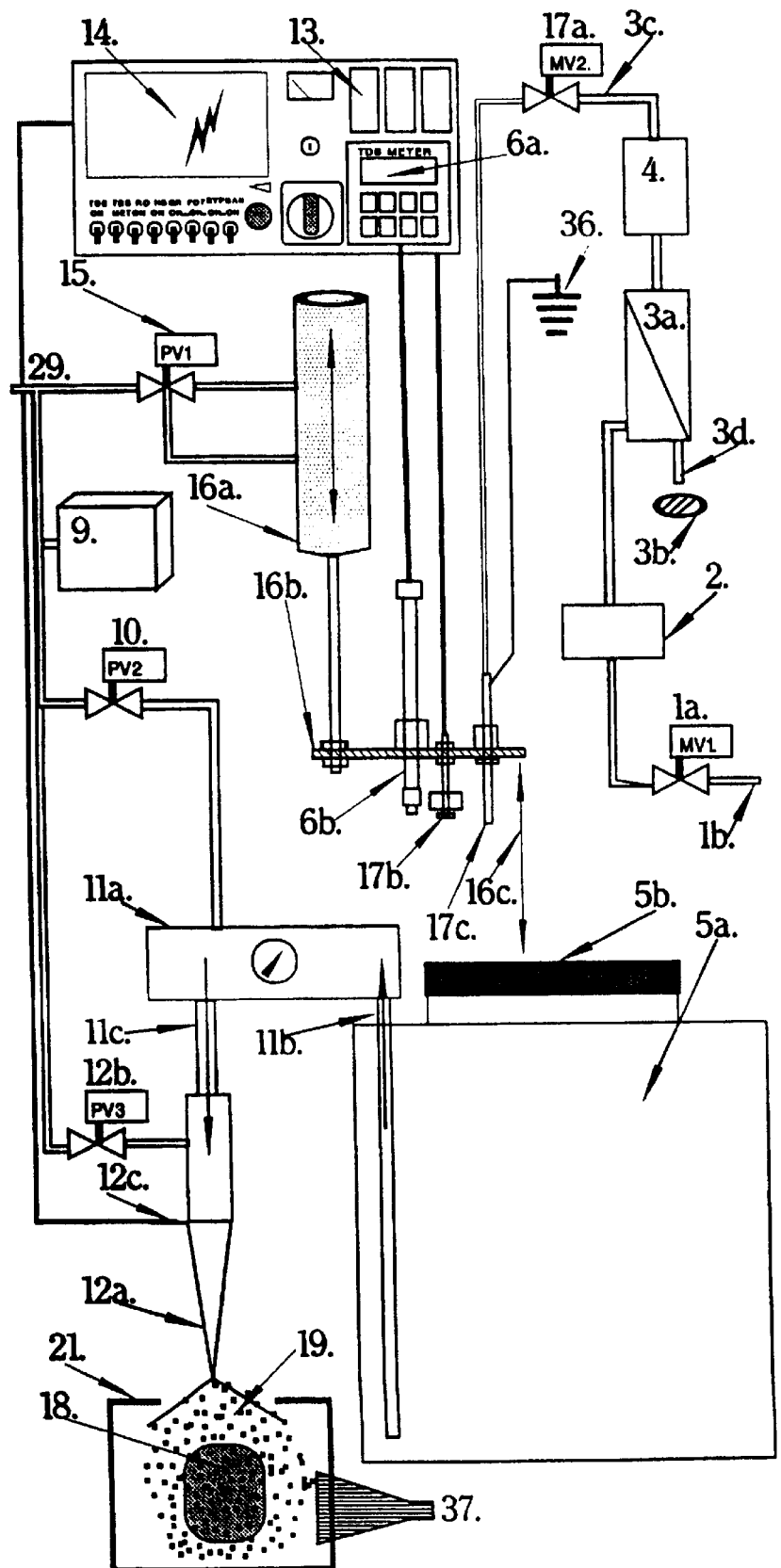
FIG. 1 shows in a block diagram the plant designed to implement the method according to the invention.
Figure 2:
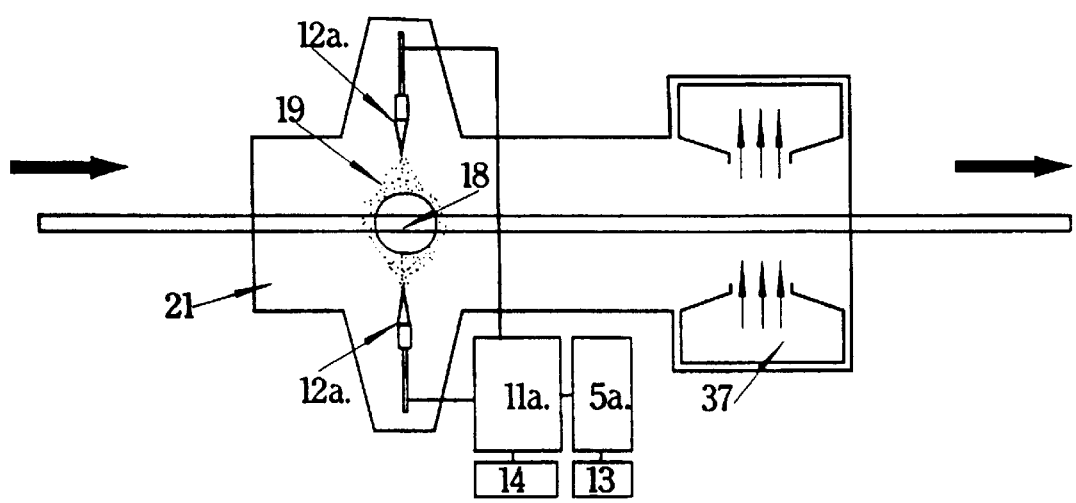
FIG. 2 shows a schematic top view of the plant shown in FIG. 1.

As shown in FIG. 1, an installation for implementing the method according to the invention comprises a control cabinet 13 and a treatment cabinet 21. The installation generates steam from tapwater admitted through magnetic valve 1a from inlet 1b, and treated by deionizer 2. reverse osmosis thermal treater 3a having an outlet 3b, permeat outlet 3c and concentrate outlet 3d. The treatment line also includes a buffer pressure tank 4 for desalinated water and a magnetic valve 17a for admission of water to the buffer tank 5a having a lid 5b. Control cabinet 13 includes a monitor 6a connected to a probe gauge 6b mounted on chassis 16b with a level gauge 17b and an inlet branch for water intake 17c, connected to a ground 36. The chassis level is controlled by a two-way air cylinder 16a, which is also connected to an inlet for compressed air 29 through a magnetic valve 15. The compressed air is supplied by an air compressor 9, which is also connected to steam generator 11a through a magnetic valve 10 for steam pressure ON, and to electric pole 12c through valve 12b for start/stop of steam intake. The electric pole 12c is connected to the steam generator 11a through outlet 11c. Steam generator 11a is connected to water tank 5a through an intake 11b.

Inside the cabinet 21. items of food, feeds or other articles are, by means of steam, exposed to a surface temperature of more than 50° C. within a defined interval, in such a combination as can be selected and determined so as to kill micro organisms, germs or viruses.

The rise in temperature on the surfaces exposed is achieved under influence of aqueous steam, or in certain instances vapors from other suitable liquids, which steam will condense on the surface of the foods, feeds or other products, in such a way that the steam is led onto the surface from steam generator 11a, which discharges steam to a steam injector 12a. Inside the steam injector, steam is led through an electric field which is established between an electric terminal that may be mounted in the steam injector and a grounded item 18. The potential in the potential field will transport the steam from the steam injector 12a onto the surface of the item 18 within a very short time and will ensure that the condensed steam is evenly dispersed over the surface of the item in question.

By the method according to the invention the item 18 which is to be disinfected/sterilized is grounded, and it is treated in a period of time, at a temperature and at an electric potential which in each case is sufficient to ensure the killing of germs or bacteria. The period of time can be controlled by aid of the speed of movement of the item to be treated, phase of treatment, rotation of the item, or other time related factors, and temperatures achievable are controlled by the outlet temperature of the generator steam, which generator according to the invention may be a low pressure generator with a temperature up to the boiling point of the water/liquid, or it may be a high pressure generator with temperatures above the boiling point of the water/liquid. In that way the steam may contain the quantity of heat necessary to carry out the disinfection/sterilization and heat may be transported to the surface of the item either by thermal conduction or by release of condensed heat, which amount to multiples of the specific heat of steam of waters/liquids.

The static electric potential field is shaped and established in accordance with the size of the surfaces, shapes and structure of the item to be treated, in such a way that the heat transfer by condensing steam becomes uniform on the item surfaces as desired. The electrostatic field is charged with a potential which can be chosen from 1000 V and upwards, and the items to be treated are earthed while an electric pole for positive or negative electric charge is mounted in relation to the outlet of the steam generator so that the electric field may accelerate the steam ejected onto the surface of the item at great speed and evenly dispersed without essential loss of speed and without essential loss of heat to the surrounding mass of air.

The upper limitation of the potential field is decided by practical, theoretical, workplace and insulation conditions, and other physical conditions plus the proper regards to work with high voltage static electricity.

In the method according to the invention a thin layer of condensed steam of water/liquid is formed on the surface of the item to be treated, which surface is heated to the calculated temperature for the task at a calculated depth. After treatment according to the method of the invention, the temperature will at once be reduced to that of the level of the item treated on account of the relatively large heat capacity of the item. The thermal effect by means of the condensed steam on the surface of the item is so intensive that the actual surface is only heated in very limited calculated depth during the chosen interval at the desired temperature. The chosen intensity of the heat treatment is selected in order that all bacteria and germs are killed, whereas the item surface is not affected by the treatment, neither in appearance nor structure.

The magnetic valve 10 for the steam generator 11a controls emission of calculated amounts of steam. The steam generator 11a produces the volume of steam desired while taking in the water/liquid from the tank 5a through the pipe 11b, and the steam produced is led to the steam injector 12a through a pipe 11c. Surplus water/liquid amounts are taken back to the tank 5a through a pipe not shown in the drawing.

The steam is ejected and dispersed in a desired fan or cone or other suitable geometric shape through the pipe opening or nozzle (steam injector) 12a, and the influx of steam is controlled by valve 12b. The electric potential is imposed on the steam spray/fan/cone through electric pole 12c. The electric potential field is shaped by placing the electric pole inside, by or in front of the injector 12a and by simultaneous grounding of the item, and also by the positioning of said item inside the cabinet 21 and/or by transportation through certain regions in the area or through the surrounding space in front of the steam ejection unit.

The surface of the item to be treated receives the condensation product of the steam, which condensate amount. is small considering the calculated treatment interval, steam temperature and distance between steam ejector and item, so that the condensate will quickly evaporate from the surface of the item or will be removed with dry or heated air from a ventilation unit 37.

A physical/mathematical survey of the transportation of mass in connection with the disinfection or sterilization of food articles is shown in the following Table 1:

|  | Meat Tissue Heating | Thickness | Area $m^2$ | kcal/kg/ °C. | kcal/80° C. | Theor. temp rise |
|---|---|---|---|---|---|---|
|  | 100 mym Condensate | 0.1 mm mm | 1 $m^2$ | 0.9 kcal/kg | 7.2 kcal/$m^2$ | t° C. |
| steam | 50 mym | 0.05 | 1 | 580 | 29.0 | 322 |
| steam | 25 mym | 0.025 | 1 | 580 | 14.5 | 15 |
| steam | 15 mym | 0.015 | 1 | 580 | 8.7 | 97 |
| steam | 10 mym | 0.01 | 1 | 580 | 5.8 | 64 |

A theoretical thickness of the condensate layer of 15 mym aqueous steam (580 kcal/kg) will be sufficient for a temperature increase of 97° C. on the surface of the item, which has a heat capacity of 0.9 kcal/kg/° C. Rises in temperature above that of the boiling point of a liquid can only be effected by means of superheated steam.

This theoretical calculation shows that the thickness of the layer or the relative weight of the steam concentrate on the surface of the item is directly proportional to the tame interval, item speed, steam capacity, distribution area, steam temperature (superheated as compensation for the heat loss during transmission from steam injector to the item), distance of item from steam injector, and the intensity of the electric potential field. The surface temperature and the duration of exposure thereto may be altered and controlled at any level, matching the intensity of disinfection or sterilization desired in order to achieve a specific or general killing of germs or bacteria or virus termination.

EXAMPLE 1

One experiment was carried out with a standard configuration so that all parameters could be varied. Pieces 10 of pork meat were placed and [earthed] grounded on [the] a conveyor which could be moved at varying speeds. [The] An electric potential field could be varied from 1 KV [and] upwards, while a steam spray was injected from the injector 12a at 100° C. Initially, the steam cloud spread out from the injector, but at increased potential above 5000 V the steam cloud gathered to follow the field lines of the electric potential field and to move at great speed towards the item treated and settled evenly on the surface of the item 18.

At each experiment the heat supply to the steam generator and the intensity of the electric potential field were varied, corresponding to a certain speed of the conveyor supporting the item, in order that the same amount of condensed steam/water per area unit could be achieved. In the first series of experiments visual evaluation was used to assess the capability of the surface to hold on to the condensate layer without "spills", but later series were made with weighing of the items immediately before and after passage through the cabinet 21 with exposure to the steam injector, since 0.1 mm layer of water corresponds to 100 g/$m^2$ or 2000 grams per 0.02 $m^2$, which could be controlled with a high degree of certainty. The experiment thus showed with certainty that transmission of thermal effect to the surface of the item could be predetermined and controlled.

EXAMPLE 2

The configuration from Example 1 was used again for this experiment, as the temperatures achieved were the subject of measuring. Using thermometers to assess temperatures on such thin layers of the item is not possible in this instance (0.01 to 0.1 mm). Therefore, temperature measurements by infrared heat radiation was chosen, a process that can be carried out with good certainty of measurement and reproducible properties. The temperature increase on the surface of the item followed steam amounts and exposure interval in the temperature area directly proportionally up to some 100 to 105° C., after which proportionality decreased at rising temperature. This was true for all practical conveyor speeds, corresponding controlled steam doses, intensities of the electric potential field, and spreading of the steam spray to the extent that a visible wrap around or fluctuation of the vapor transmission by means of the electric field were evident. The electric voltage in this second experiment was varied up to 90,000 V and it was remarkable that the steam emission from the injector became more and more invisible at rising electric field intensity, which is caused by faster steam particle transmission, less cooling during the transmission, and consequent less condensation. In the temperature interval 90 to 100° C. the loss of transmission effect was in the area of 20 to 40% of the values theoretically achievable.

EXAMPLE 3

For this third experiment several parameters were fixed beforehand in order to ensure that, at certain temperatures, and at certain intervals, bactericidal effects could be ascertained on specific strains of bacteria. The intention of this present invention is that both disinfection and sterilization should be achievable for specific types of bacteria, but considering the overlap of these concepts definitions have to be set up first:

Sterilization is a procedure which aims at removing, deactivating or killing all micro organisms, i.e. to achieve sterility. Sterility is an absolute concept.

Figure 6:
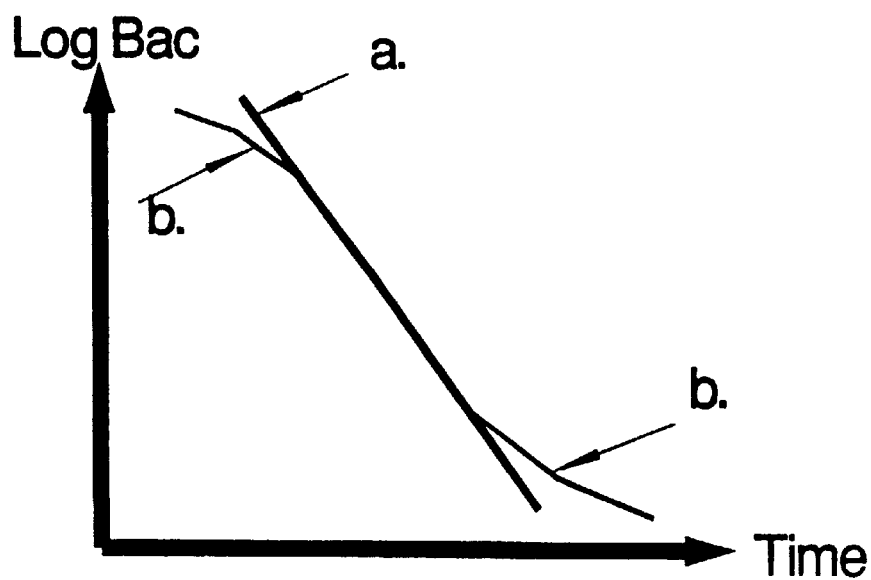
FIG. 6 shows a calculated bactericide graph and an experimental bactericide graph.

Disinfection is a procedure which aims at removing, deactivating or killing certain defined groups of micro organisms to a proper extent seen in relation to the purpose. Disinfection is a relative concept. In FIG. 6, graph a shows an idealized chain of events in terms of bactericidal effect, and graph b shows the actual chain of events.

The extent of bactericidal effect in the case of pathogenic bacteria is 95 to 98% in connection with food or [feeding stuff] feed technology.

Figure 4:
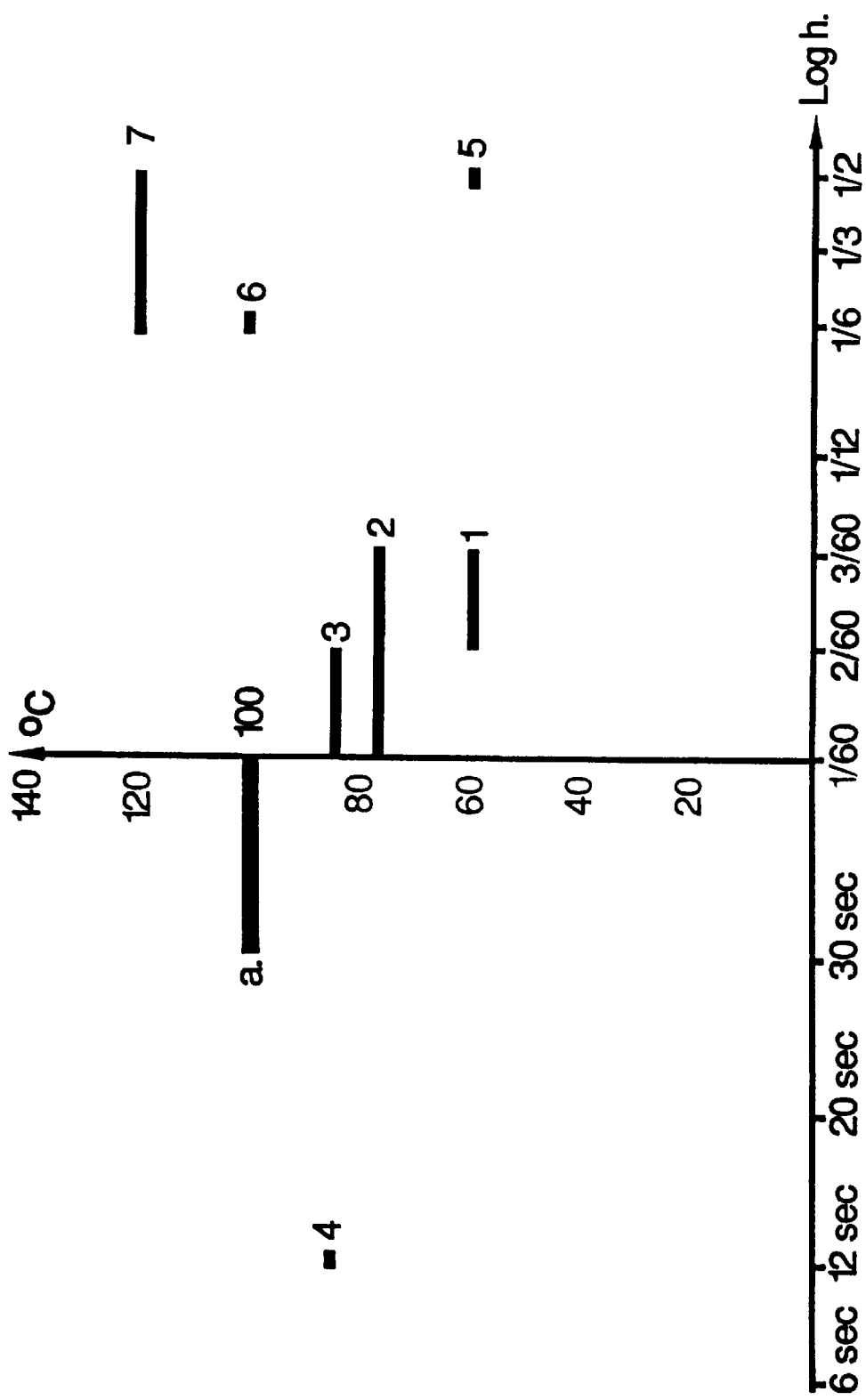
FIG. 4 shows a diagram of the disinfection process for different products.

Disinfections are used in the food business for several purposes, and some practical examples are shown in FIG. 4, where:

graph 1 shows the chain of events when disinfecting for bacteria, fungi and viruses for 2–3 minutes at 50 to 60° C., graph 2 shows the chain of events when disinfecting in various food processing plants at 76° C. for 1–3 minutes, graph 3 shows the chain of events when disinfecting in slaughterhouses for 1 to 2 minutes at 82° C., graph 4 shows the chain of events when preserving fruit juice (soft drinks) for 11 seconds at 85° C., graph 5 shows the chain of events when pasteurizing against salmonella typhoid for 30 minutes at 62° C., graph 6 shows the chain of events in disinfection of doctors' apparatus (killing of pathogenic bacteria) for 10 minutes at 100° C., graph 7 shows the chain of events in a doctor's autoclave disinfection for 10 to 30 minutes at 100° C., and graph a shows the chain of events according to this present invention, Example 3, for 30 to 60 seconds at 100° C.

The bactericidal effect depends on both time of exposure and of temperature, and initial experiments covering combinations of these two variables decided the final parameters of the experiment. It is common experience in the 10 food technology business that fast heating and cooling will make disinfection more efficient compared to slow changes of temperature, a fact which explains the large variation in disinfection temperatures chosen in various types of processing plants.

Figure 5:
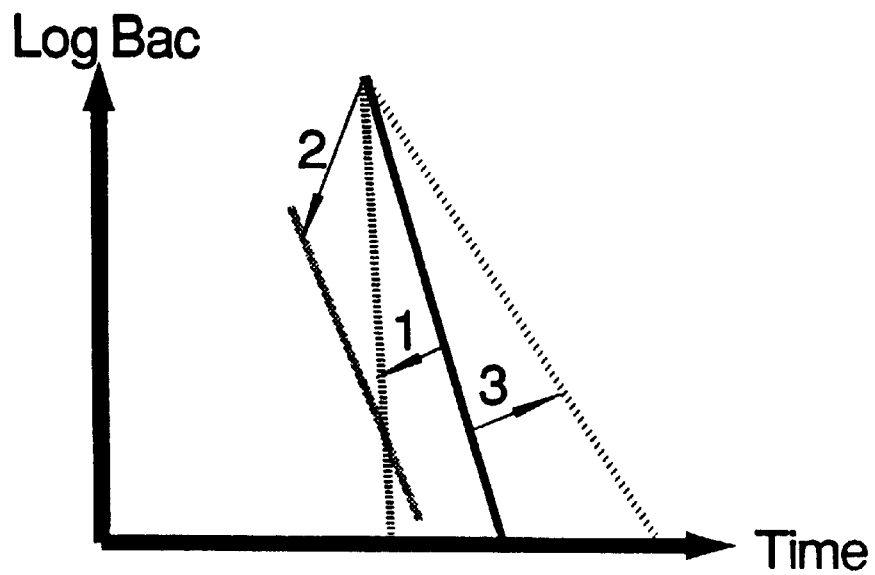
FIG. 5 shows graphs describing the correlation between bactericide and treatment time and temperature in the disinfective process.

As shown in FIG. 5 the count of bacteria ideally falls exponentially in relation to the time of exposure used. As indicated at arrow 1 the time of sterilization is reduced in accordance with increased dosage of sterilization agent. As indicated at arrow 2, the time of sterilization is reduced at reduced germ count, and as indicated at arrow 3, some bacteria are more resistent than others, whereby the exposure needed is increased.

The configuration from Example 2 was used again for Example 3, and considering the prime purpose of sterilizing/ disinfecting the surface of the item, the experiment was made using oval-shaped cuts of pork with diameters of 8 to 11 cm, thickness 2 cm, which results in an aggregate surface of all sides to be involved in the exposure of 1.3 $dm^2$. 11 pieces of pork were infected, using a spatula, with bacteria of the Cereus type, a strain that is regarded as having the same resistance to temperature as salmonella.

The water steam generator 11a was set for delivery of steam onto a surface of 1.5 dm at a distance of 0.5 dm, and the steam generator was adjusted to a steam yield of 5 grams per minute, which theoretically when calculating a heat loss >50% corresponds to a heat exposure of the surface at 100° C. for 60 seconds. The high electric potential field was set at a voltage drop of 80 kV between the negative pole at the steam ejector and the grounded item to be treated.

With this setting, the cut of pork mentioned above was brought by conveyor into the exposure area, centered and brought to a standstill, exposed to aqueous steam treatment for 60 seconds, and then conveyed out of the electric field at a speed of 0.5 cm per second. At the same time, the infrared radiation temperature reading proved that temperatures of between 97 and 102° C. had been achieved during the exposure (shown graphically in FIG. 4).

After this treatment, the next step in the experiment was to ascertain the extent of the bactericidal effect.

Figure 3:
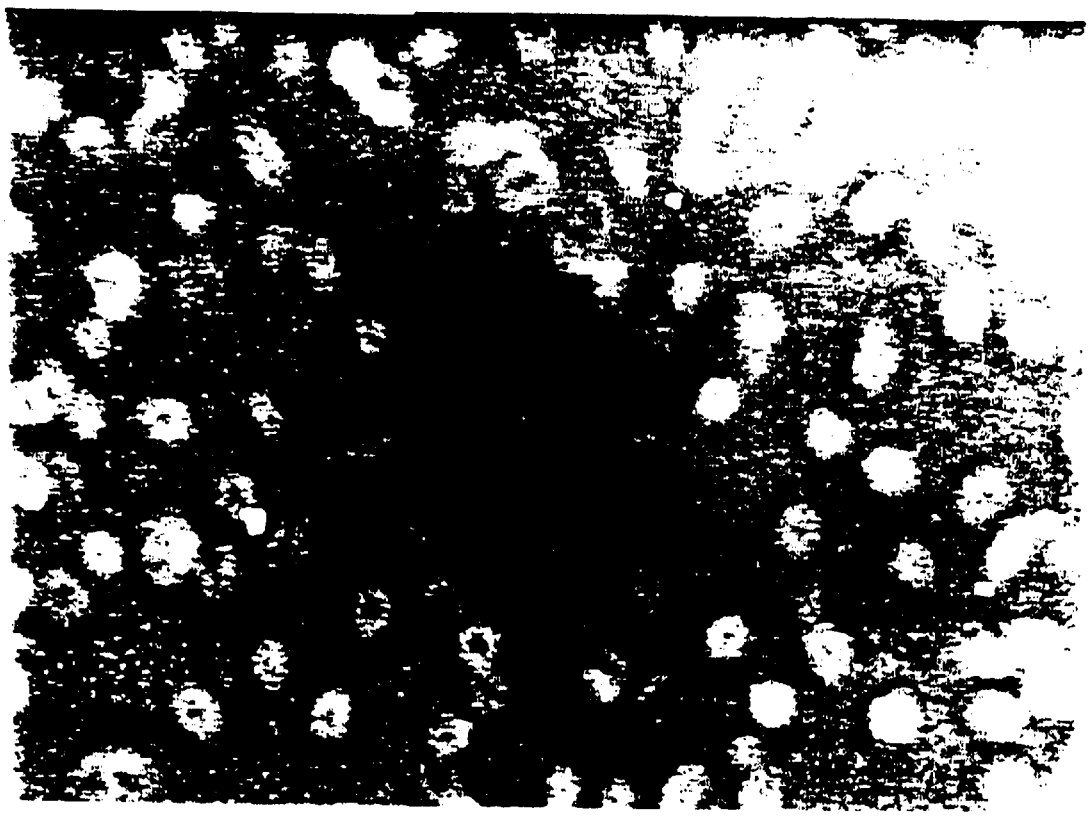
FIG. 3 shows a picture of bacteria seen in a microscope.

In consideration of the numerous analyses of the bactericidal effects the laboratory was provided with a microscope with a magnification of 800×, fitted with a camera and a 14" monitor so that bacteria could be watched over a 24 hour period for signs of life. These signs of life were determined by the ability of the bacteria to divide or propagate. The images of the bacteria were shown in approx. 10 mm diameter, i.e. 2000 times magnification (FIG. 3).

After treatment, areas of 5 $cm^2$ were moistened with pure clean water, and the water was collected by pipette and a sterile substrate for growth (broth or meat soup) was added, and this mixture was deposited in pipette tubes, 0.02 mm aperture. The pipette tube was sealed at the ends and placed under a microscope. The liquid was contained and the bacteria thus trapped could be identified in the field of vision, containing some 10 to 90 bacteria. A count ensured that propagation, if any, could be ascertained.

A count taken 24 hours later proved that no bacteria had propagated or divided, and disinfection had therefore been 100% efficient. By definition, sterilization is an absolute concept, and scientific proof would demand a very extensive statistical material which could be created only in actual use, since sterilization according to scientific specifications is achieved at 121° C. for 10 to 30 minutes in superheated aqueous steam, with dosages as desired (aguaous steam at 120° C. will be achieved at 1.99 bar and at 130° C. at 2.70 bar).

This experimental series was concluded with 10 continuous tests. In the first 5 tests, temperature and exposure intervals were kept at 97–102° C. and 60 seconds, with a count of bacteria which averaged 67 at the counting, of which none showed signs of life in the aforesaid 24 hours at 37° C., and in the next 5 tests with an average of 73 bacteria and 30 seconds of exposure at the same temperature. None of the bacteria showed signs of life in the following 24 hours at 37° C. FIG. 3 shows a section of a control field with bacteria.

Control of the reliability of the experiments were made with a piece of meat which was not exposed to heat. After a time lapse corresponding to the average time needed for the experiments indicated in the above pipette samples were taken from the surface bacteria as described, and a bacteria count over 24 hours showed that the bacteria count has multiplied many times over, which fact proved the growth conditions in the growth substrate used.

On the basis of the experimental results indicated in the above the bactericidal effects were entered in FIG. 4. Experiments made in the test series under similar conditions, but at shorter exposures, showed that a reduction of the time or interval for the thermal treatment meant that propagation of bacteria would be possible. Discovery of initial bacteria growth will depend on many intricate parameters in the test series. For this present invention it is of importance to ascertain that the continued life of bacteria can be proven when using certain short period or interval heat treatment, and that one—if one uses a suitable and determined length of the interval in question—may achieve a disinfection rate which in efficiency approaches asymptotically a rate of 100 per cent.

According to the invention less aqueous (liquid) steam is used and thereby less energy for disinfection or sterilization than with other heat-dependent disinfection methods, since the loss of thermal energy is minimized in order that a very large percentage of the steam used contributes to creating thermal effects on the surface of the item to be treated, transmitted to a very thin layer and not transmitted to surrounding masses of air or devices. In the embodiment specified the invention will keep neighboring workplaces free of steam exhaust via the electrostatic field established for the purpose.

The configuration, plant or embodiment here shown only serves as one example for the implementation of the method according to the invention.

what is claimed is:

1. A method for disinfection or sterilization of food articles or machinery, comprising the steps of:

electrically grounding an item of food or machinery to be disinfected or sterilized;

generating vapor from water or other liquid substance;

directing the vapor through an electrostatic potential field of defined shape generated with an electrostatic high voltage, whereby the vapor assumes the shape of the field with an electrostatic potential imposed thereon; and exposing the grounded item for a predetermined time to the vapor having the electrostatic potential applied thereto at a temperature above 50° C.

2. A method according to claim 1, wherein said electric potential field is established at high voltage exceeding 1 kV.

3. A method according to claim 1, wherein the vapor comprises evaporated water, liquids, liquid mixtures, or liquids containing dissolved gases or gaseous substances.

4. A method according to claim 1, wherein the vapor is generated below the boiling point of the water or liquid, at the boiling point, or above the boiling point to produce superheated vapor, in order to achieve a desired temperature level for the vapor or a thermal effect.

5. A method according to claim 4, wherein the liquid is water.

6. A method according to claim 5, wherein the vapor is saturated steam generated below the boiling point of the water, or superheated steam generated above the boiling point of the water.

7. A method according to claim 1, wherein the electric field has a potential of about 1 kV to 200 kV.

8. A method according to claim 1, wherein the vapor is generated from a liquid comprising an organic liquid or liquid mixture.

9. A method according to claim 8, wherein the organic liquid is an alcohol or an acid.

10. A method according to claim 1, wherein the liquid comprises an inorganic liquid or liquid mixture.

11. A method according to claim 10, wherein the inorganic liquid is hydrogen peroxide.

12. A system for disinfection or sterilization of food articles or machinery, comprising:

a cabinet with an electrically grounded conveyor means, constructed and arranged for conveying an item to be disinfected or sterilized at a desired speed through said cabinet;

a vapor generator for generating vapor from water or other liquid and having an outlet for the vapor;

a vapor injector connected to the vapor generator and being constructed and arranged for injection of vapor into the cabinet;

a source of electrostatic high voltage having an electrode disposed in a vapor path including the injector and the cabinet, such that the vapor becomes electrostatically charged and assumes a predetermined pattern within the cabinet for treatment of the item with charged vapor;

a ventilation unit connected to the cabinet for treatment of the item subsequent to treatment of the item with the charged vapor.

13. An system according to claim 12, wherein the vapor injector comprises an injection nozzle, a geometrical pipe opening, or a mass regulating flow diameter or cross sectional area.

14. An system according to claim 12, wherein the vapor injector comprises at least one electrode connected to the source of electrostatic high voltage.

* * * * *